(12) United States Patent
Dion et al.

(10) Patent No.: US 11,963,875 B2
(45) Date of Patent: Apr. 23, 2024

(54) ORTHOPAEDIC PROSTHESIS FOR AN INTERPHALANGEAL JOINT AND ASSOCIATED METHOD

(71) Applicant: DEPUY SYNTHES PRODUCTS, INC., Raynham, MA (US)

(72) Inventors: Donald Dion, Warsaw, IN (US); Chad Lawrence, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 204 days.

(21) Appl. No.: 17/370,511

(22) Filed: Jul. 8, 2021

(65) Prior Publication Data

US 2021/0330462 A1    Oct. 28, 2021

Related U.S. Application Data

(62) Division of application No. 15/808,418, filed on Nov. 9, 2017, now Pat. No. 11,071,630.

(51) Int. Cl.
*A61F 2/42*    (2006.01)
*A61B 17/00*   (2006.01)
*A61F 2/30*    (2006.01)

(52) U.S. Cl.
CPC ........ *A61F 2/30771* (2013.01); *A61F 2/4241* (2013.01); *A61F 2002/30069* (2013.01); *A61F 2002/30138* (2013.01); *A61F 2002/30141* (2013.01); *A61F 2002/30143* (2013.01); *A61F 2002/30148* (2013.01); *A61F 2002/30151* (2013.01); *A61F 2002/3028* (2013.01); *A61F 2002/30593* (2013.01); *A61F 2002/30818* (2013.01); *A61F 2002/3082* (2013.01); *A61F 2002/30827* (2013.01); *A61F 2002/30828* (2013.01); *A61F 2002/3092* (2013.01);
(Continued)

(58) Field of Classification Search
None
See application file for complete search history.

(56) References Cited

U.S. PATENT DOCUMENTS 3,593,342 A * 7/1971 Niebauer .............. A61F 2/4241
                                                  623/21.11
3,824,631 A * 7/1974 Burstein ................ A61B 17/68
                                                  623/23.39
(Continued)

FOREIGN PATENT DOCUMENTS

GB      2458218 A       9/2009
WO      9740786 A1      11/1997
WO      2013006778 A2   1/2013

OTHER PUBLICATIONS

PCT International Search Report for International Application No. PCT/IB2018/058777, dated Feb. 21, 2019, 9 pages.
(Continued)

*Primary Examiner* — Ann Schillinger
(74) *Attorney, Agent, or Firm* — Barnes & Thornburg LLP

(57) ABSTRACT

An orthopaedic prosthesis is disclosed. The orthopaedic prosthesis includes a frame including a plurality of beams defining an open-cell structure and a shell applied to the frame. The frame includes a proximal arm, a distal arm, and a central body connecting the proximal arm to the distal arm. The shell extends over the proximal arm, the distal arm, and the central body of the frame. A method of implanting an orthopaedic prosthesis is also disclosed.

8 Claims, 5 Drawing Sheets

(52) U.S. Cl.
CPC ............... *A61F 2002/30971* (2013.01); *A61F 2002/30985* (2013.01); *A61F 2002/4243* (2013.01); *A61F 2310/00011* (2013.01)

(56) References Cited

U.S. PATENT DOCUMENTS

| | | | | |
|---|---|---|---|---|
| 3,886,600 A * | 6/1975 | Kahn | ............... | A61F 2/30907 |
| | | | | 128/DIG. 21 |
| 4,578,080 A * | 3/1986 | Helal | ............... | A61F 2/4241 |
| | | | | 606/155 |
| 4,871,367 A * | 10/1989 | Christensen | ......... | A61F 2/4241 |
| | | | | 623/21.15 |
| 5,011,497 A * | 4/1991 | Persson | ............... | A61F 2/4241 |
| | | | | 623/23.41 |
| 5,108,443 A * | 4/1992 | Branemark | ........... | A61F 2/4241 |
| | | | | 606/66 |
| 5,824,095 A * | 10/1998 | Di Maio, Jr. | ......... | A61F 2/4241 |
| | | | | 623/18.11 |
| 5,984,970 A | 11/1999 | Bramlet | | |
| 6,206,924 B1 * | 3/2001 | Timm | ............... | A61F 2/28 |
| | | | | 623/17.11 |
| 6,319,284 B1 * | 11/2001 | Rushdy | ............... | A61F 2/4225 |
| | | | | 623/21.19 |
| 6,869,449 B2 * | 3/2005 | Ball | ............... | A61F 2/4241 |
| | | | | 623/21.11 |
| 8,852,284 B2 * | 10/2014 | Wiley | ............... | A61F 2/4241 |
| | | | | 623/20.15 |
| 9,456,901 B2 * | 10/2016 | Jones | ............... | C23C 4/02 |
| 9,907,657 B2 * | 3/2018 | Fonte | ............... | A61F 2/4455 |
| 11,071,630 B2 * | 7/2021 | Dion | ............... | A61F 2/30771 |
| 2002/0169066 A1 | 11/2002 | Cassidy et al. | | |
| 2003/0069645 A1 * | 4/2003 | Ball | ............... | A61F 2/4241 |
| | | | | 623/18.11 |
| 2005/0169893 A1 * | 8/2005 | Koblish | ............... | A61L 27/56 |
| | | | | 424/602 |
| 2007/0185583 A1 * | 8/2007 | Branemark | ........... | A61F 2/4241 |
| | | | | 623/18.11 |
| 2010/0161061 A1 * | 6/2010 | Hunt | ............... | A61B 17/1604 |
| | | | | 623/16.11 |
| 2013/0218282 A1 | 8/2013 | Hunt | | |
| 2015/0223942 A1 * | 8/2015 | Merle | ............... | A61F 2/4637 |
| | | | | 606/86 R |
| 2017/0095337 A1 * | 4/2017 | Pasini | ............... | A61F 2/36 |
| 2018/0368981 A1 | 12/2018 | Mattes et al. | | |

OTHER PUBLICATIONS

DePuy Synthes, NeuFlex MCP/PIP Finger Joint Implant Systems, Surgical Technique, published Mar. 2015, 8 pages.

* cited by examiner

ORTHOPAEDIC PROSTHESIS FOR AN INTERPHALANGEAL JOINT AND ASSOCIATED METHOD

The present application is a divisional application of U.S. Application Ser. No. 15/808,418, now U.S. Pat. No. 11,071,630, entitled "ORTHOPAEDIC PROSTHESIS FOR AN INTERPHALANGEAL JOINT AND ASSOCIATED METHOD," which was filed on Nov. 9, 2017, the entirety of which is hereby incorporated by reference.

TECHNICAL FIELD

The present disclosure relates generally to prosthetic joint components, and more particularly to, prosthetic joint components for use in various extremities.

BACKGROUND

Orthopaedic prostheses for extremity joints, particularly interphalangeal or metacarpophalangeal, are used to replace natural joints compromised by degenerative or inflammatory joint disease, dislocation of the joints, or other painful joints having limitation of motions. Adequate bone stock and lack of infection are typically also required.

Interphalangeal joint prostheses typically employ two intramedullary stems or arms with a pivoting unit located therebetween. The pivoting unit includes a dorsal concavity and in some cases a small palmar concavity. The concavities provide a "weak" spot that encourages the location of the pivoting deformation to the hinge, thereby producing predictable and natural motion. Exemplary interphalangeal joint prostheses are shown and described in U.S. Pat. Nos. 6,869,449 and 5,984,970, which are expressly incorporated herein by reference.

SUMMARY

According to one aspect of the disclosure, an orthopaedic prosthesis is disclosed. The orthopaedic prosthesis comprises a frame including a plurality of beams defining an open-cell structure and a shell that encases the frame. The frame includes a proximal arm, a distal arm, and a central body connecting the proximal arm to the distal arm. The central body includes a first groove and a second groove positioned opposite the first groove to permit flexion motion between the proximal arm and the distal arm. The shell extends over the proximal arm, the distal arm, and the central body of the frame.

In some embodiments, the open-cell structure may include a plurality of polyhedrons, and each polyhedron may include a plurality of openings surrounding a central cavity. The plurality of polyhedrons may be edge-transitive convex polyhedrons. In some embodiments, the plurality of polyhedrons may be rhombic dodecahedrons.

In some embodiments, the shell may be a silicone coating applied to the frame. Additionally, in some embodiments, the frame may be a single, monolithic component formed of silicone.

In some embodiments, the central body may include a first arcuate section and a second arcuate section that partially define the first groove. The central body may include a third arcuate section that is positioned opposite the first and second arcuate sections that partially defines the second groove.

The central body may include a first inner surface that includes a plurality of openings and extends from the first arcuate section toward a groove opening of the first channel to partially define the first channel. The central body may include a second inner surface that includes a plurality of openings and extends from the second arcuate section toward the groove opening of the first channel to partially define the first channel. The central body may include a third inner surface and a fourth inner surface that each include a plurality of openings and extend from the third arcuate section toward a groove opening of the second groove to partially define the second groove According to another aspect of the disclosure, an orthopaedic prosthesis is disclosed. The orthopaedic prosthesis comprises a finger joint implant having a proximal end sized to be positioned in a first finger bone, a distal end sized to be positioned in a second finger bone, and a central joint connecting the proximal end and distal end. The finger joint implant further comprises a frame extending from the distal end to the proximal end of the joint implant. The frame includes a plurality of tessellated polyhedrons that define an open-cell structure. Additionally, the finger joint implant further comprises a shell extending over the proximal end, the distal end, and the central joint to encase the frame.

In some embodiments, the plurality of tessellated polyhedrons may be rhombic dodecahedrons. In some embodiments, the shell may be a silicone coating applied to the frame. Additionally, in some embodiments, the frame may be a single monolithic component formed of silicone.

In some embodiments, the central joint may include a first channel opening in the dorsal direction and a second channel positioned opposite the first channel opening in the palmar direction to permit flexion motion between the proximal end and distal end. The central joint may include a first arcuate section and a second arcuate section adjacent the first arcuate section that partially define the first channel. The central joint may include a third arcuate section positioned opposite the first and second arcuate sections that partially defines the second channel.

In some embodiments, the prosthesis may include a reinforcing element that is positioned in the frame.

According to another aspect of the disclosure, a method of implanting an orthopaedic prosthesis is disclosed. The method comprises removing a portion of a first phalangeal bone of a patient, a portion of a second phalangeal bone, and a natural joint between the first phalangeal bone and the second phalangeal bone, inserting a proximal end of an orthopaedic prosthesis into the first phalangeal bone, and inserting a distal end of the orthopaedic prosthesis into the second phalangeal bone. The orthopaedic prosthesis includes an inner frame comprising a plurality of tessellated polyhedrons and an outer shell that encases the inner frame.

In some embodiments, inserting the proximal end of the orthopaedic prosthesis may include engaging the outer shell of the orthopaedic prosthesis with the patient's tissue. Inserting the distal end of the orthopaedic prosthesis may include engaging the outer shell of the orthopaedic prosthesis with the patient's tissue.

In some embodiments, the method of implanting an orthopaedic prosthesis may further comprise making the inner frame via a stereolithographic process. In some embodiments, the method of implanting an orthopaedic prosthesis may further comprise coating the inner frame with the outer shell. In some embodiments, the plurality of tessellated polyhedrons may include rhombic dodecahedrons.

BRIEF DESCRIPTION OF THE DRAWINGS

The detailed description particularly refers to the following figures, in which.

DETAILED DESCRIPTION OF THE DRAWINGS

Figure 1:
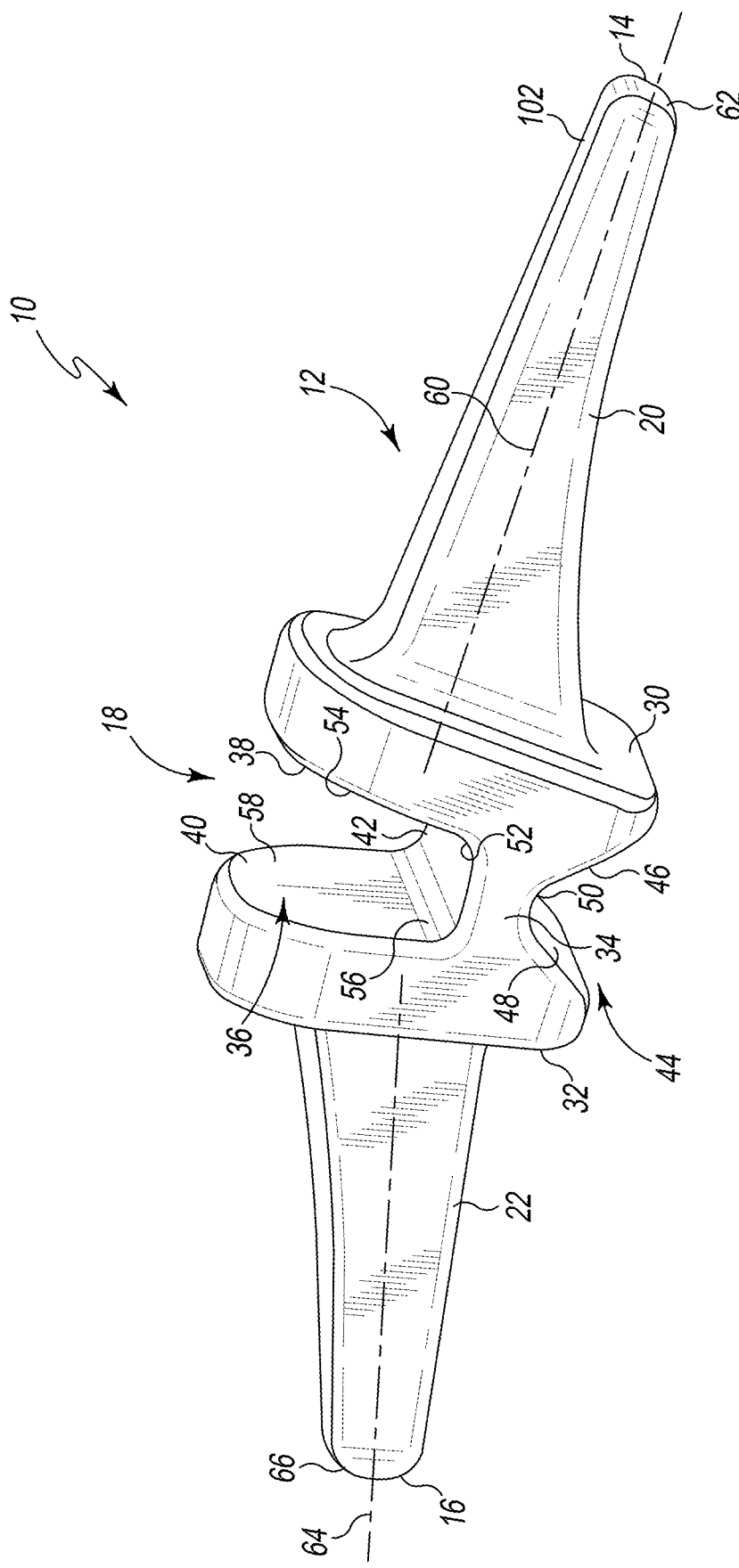
FIG. 1 is a perspective view of one embodiment of an orthopaedic prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, palmar, dorsal, etcetera, may be used throughout this disclosure about both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIG. 1, the orthopaedic prosthesis 10 to replace an interphalangeal joint of a patient's finger includes an implant 12 that extends from a proximal end 14 to a distal end 16. A central component 18 configured to permit the ends 14, 16 to move relative to one another is positioned between the ends 14, 16. The implant 12 includes a proximal stem 20 that extends from the proximal end 14 to the central component 18 and a distal stem 22 that extends from the distal end 16 to the central component 18. As described in greater detail below, the proximal end 14 and stem 20 are configured to be implanted into a proximal phalange 202 (see FIG. 5) and the distal end 16 and stem 22 are configured to be implanted into a middle phalange 204 (see FIG. 5) during a surgical procedure to replace the proximal interphalangeal (PIP) joint of a patient's finger 206.

As shown in FIG. 1, the central component 18 includes a proximal wing 30 connected to the proximal stem 20 and a distal wing 32 connected to the distal stem 22. A bridge 34 connects the proximal wing 30 to the distal wing 32. A channel 36 is defined between the inner surfaces 38, 40 of the wings 30, 32, respectively, and the inner surface 42 of the bridge 34 on the dorsal side of the implant 12. Another channel 44 is defined between the inner surfaces 46, 48 of the wings 30, 32, respectively, and the inner surface 50 of the bridge 34 on the opposite, palmer side of the implant 12. The channels 36, 44 extend in a medial-lateral direction through the central component 18 and define weak spots at which bending may occur.

In the illustrative embodiment, the inner surface 38 of the proximal wing 30 includes an arcuate section 52 that is connected to the proximal edge of the inner surface 42 of the bridge 34. The inner surface 38 of the proximal wing also includes a substantially planar section 54 that extends dorsally from a dorsal edge of its arcuate section 52.

Similarly, the inner surface 40 of the distal wing 32 includes an arcuate section 56 that is connected to the distal edge of the inner surface 42 of the bridge 34. The inner surface 40 of the distal wing also includes a substantially planar section 58 that extends dorsally from a dorsal edge of its arcuate section 56.

As shown in FIG. 1, the inner surface 50 of the bridge 34 on the opposite, palmer side of the implant 12 is arcuate. The inner surfaces 46, 48 of the wings 30, 32, respectively, are connected at each edge of the surface 50, and extend palm-ward. In the illustrative embodiment, the inner surfaces 46, 48 are substantially planar.

It should be appreciated that the implant 12 is shown in FIG. 1 at an "at rest" position prior to implantation. The proximal stem 20 extends along a longitudinal axis 60 from a tip 62 to the proximal wing 30 of the central component 18. Similarly, the distal stem 22 extends along a longitudinal axis 64 from a tip 66 to the distal wing 32. As shown in FIG. 1, the axes 60, 64 (and hence the stems 20, 22) are angled with respect to each other prior to implantation and when the implant 12 is under no significant external force. This angle corresponds to the naturally-biased orientation of the phalanges, which can extend at angles that range from about 10° to about 50°, depending on the location of the joint. For example, the natural bias of a PIP joint of an index finger is different from the natural bias of the PIP joint of a ring finger. It should be appreciated that a suitable angle may be determined to accommodate the natural bias of any extremity.

Figure 2:
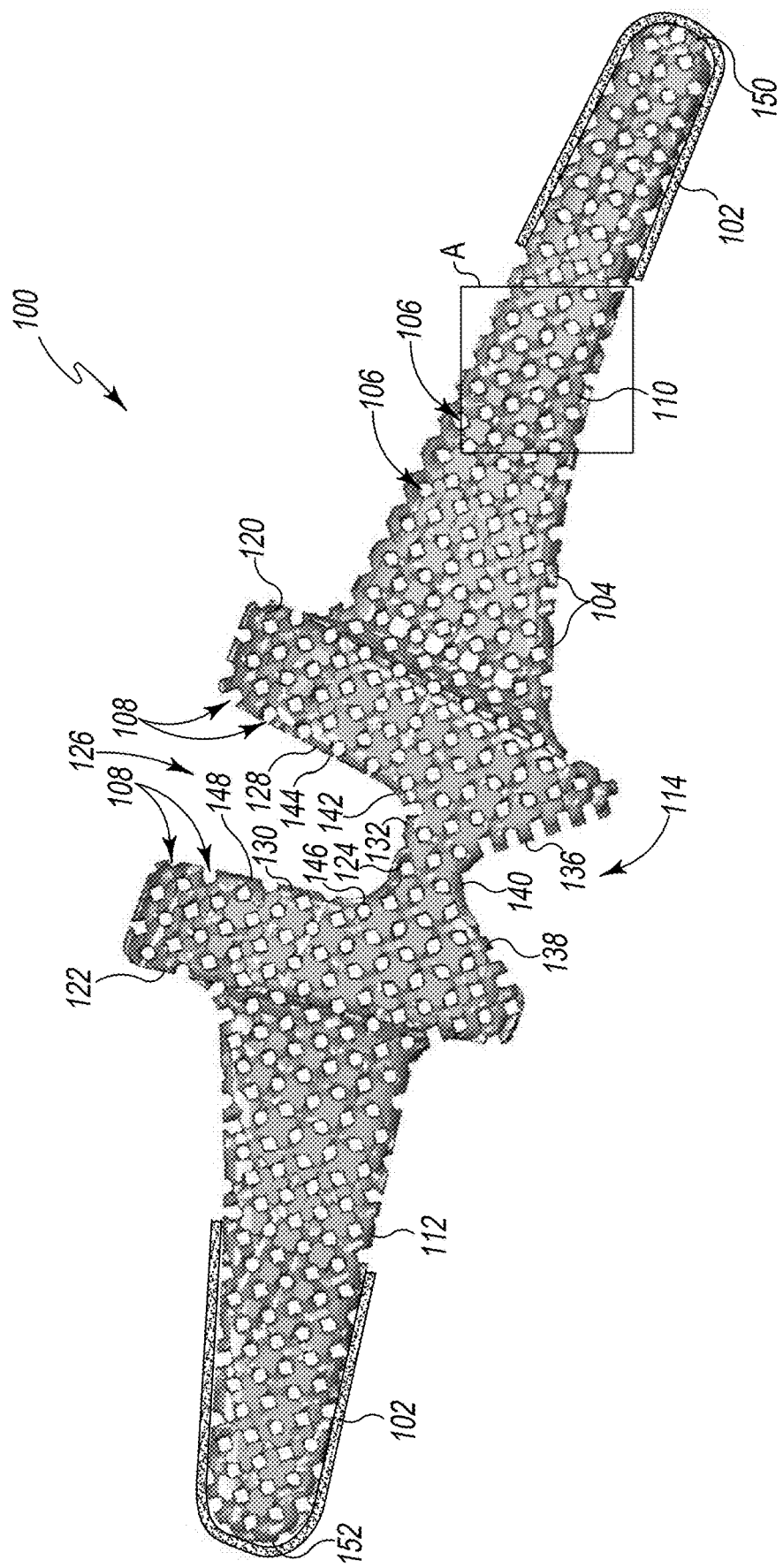
FIG. 2 is a perspective view of the orthopaedic prosthesis of FIG. 1 with the coating partially removed to show the inner frame of the orthopaedic prosthesis.

Referring now to FIG. 2, the implant 12 includes a frame 100 that is encased in an outer shell 102. The frame 100 forms the basic structure that defines the geometry of the implant 12. In the illustrative embodiment, the frame 100 is composed of a plurality of interconnected beams 104. A plurality of openings 106 are defined between the beams 104 to form an open-cell structure. The frame 100 is semi-rigid so that the implant 12 is maintained "at rest" position with the stems 20, 22 angled as described above when the implant 12 is under no significant external force. The frame 100 is formed as a single, monolithic structure from silicone. In the illustrative embodiment, the frame 100 is formed by stereolithography, which is a form of 3-D printing technology. In stereolithography, the frame 38 is formed in a layer by layer fashion using photopolymerization in which light causes chains of molecules to link, forming the polymeric structures that define the frame 100. It should be appreciated that other forms of 3-D printing technology such as, for example, optical fabrication, photo-solidification, or resin printing may be used to fabricate the frame 100. In other embodiments, the frame 100 may formed from a metallic material using a 3-D printing process or other manufacturing technique.

In the illustrative embodiment, the outer shell 102 is also formed from silicone. The shell 102 is applied after the frame 100 is formed and encases the frame 100 such that no portion of the frame 100 is exposed. In the illustrative embodiment, the shell 102 has a minimum wall thickness of about 400 micrometers. In other embodiments, the wall thickness may be 500 micrometers. It should be appreciated that the shell may be formed from polyurethane or other implant grade polymeric material.

As shown in FIG. 2, the frame 100 includes a proximal arm 110, a distal arm 112, and a central body 114 that connects the proximal arm 110 to the distal arm 112. In the illustrative embodiment, the proximal arm 110 defines the basic structure and geometry of the proximal stem 20 of the implant 12. Similarly, the distal arm 112 defines the basic structure and geometry of the distal stem 22 of the implant 12, and the central body 114 defines the basic structure and geometry of the central component 18 of the implant 12. In that way, the basic structure of the arms 110, 112 and the body 114 is identical to the structure of the stems 20, 22 and the central component 18 described above regarding FIG. 1.

The central body 114, like the central component 18, includes a proximal wing 120 connected to the proximal arm 110 and a distal wing 122 connected to the distal arm 112. A bridge 124 connects the proximal wing 120 to the distal wing 122. A channel or groove 126 is defined between the inner surfaces 128, 130 of the wings 120, 122, respectively, and the inner surface 132 of the bridge 124 on the dorsal side of the frame 100. Another channel or groove 134 is defined between the inner surfaces 136, 138 of the wings 120, 122, respectively, and the inner surface 140 of the bridge 124 on the opposite, palmer side of the frame 100. The grooves 126, 134 extend in a medial-lateral direction through the central body 114 and define weak spots at which bending may occur.

All the inner surfaces of the wings 120, 122 and the bridge 124 are defined by the beams 104 of the frame 100. Additionally, all the inner surfaces include openings, such as openings 108, of the plurality of openings 106 defined between the beams 104. In the illustrative embodiment, the inner surface 128 of the frame 100 defines the underlying structure of the inner surface 38 of the implant 12. The inner surface 128 of the proximal wing 120 includes an arcuate section 142 that is connected to the proximal edge of the inner surface 132 of the bridge 124. The inner surface 128 of the proximal wing also includes a substantially planar section 144 that extends dorsally from a dorsal edge of its arcuate section 142.

Similarly, the inner surface 130 of the distal wing 122 of the frame defines the underlying structure of the inner surface 40 of the implant 12. The inner surface 130 includes an arcuate section 146 that is connected to the distal edge of the inner surface 132 of the bridge 124. The inner surface 130 of the distal wing also includes a substantially planar section 148 that extends dorsally from a dorsal edge of its arcuate section 146.

The inner surfaces 132, 140 of the frame 100 defined the structure underlying the inner surfaces 42, 50 of the bridge 34 of the implant 12. The inner surface 132 of the frame 100 on the palmer side of the frame 100 is arcuate. The inner surfaces 136, 138 of the wings 120, 122, respectively, are connected at each edge of the surface 140, and extend palm-ward. In the illustrative embodiment, the inner surfaces 136, 138 are substantially planar.

In FIG. 2, the frame 100 is shown at the "at rest" position. The proximal arm 110 extends along the longitudinal axis 60 from a tip 150 to the proximal wing 120 of the central body 114. Similarly, the distal arm 112 extends along the longitudinal axis 64 from a tip 152 to the distal wing 122 of the central body 114.

Figure 3:
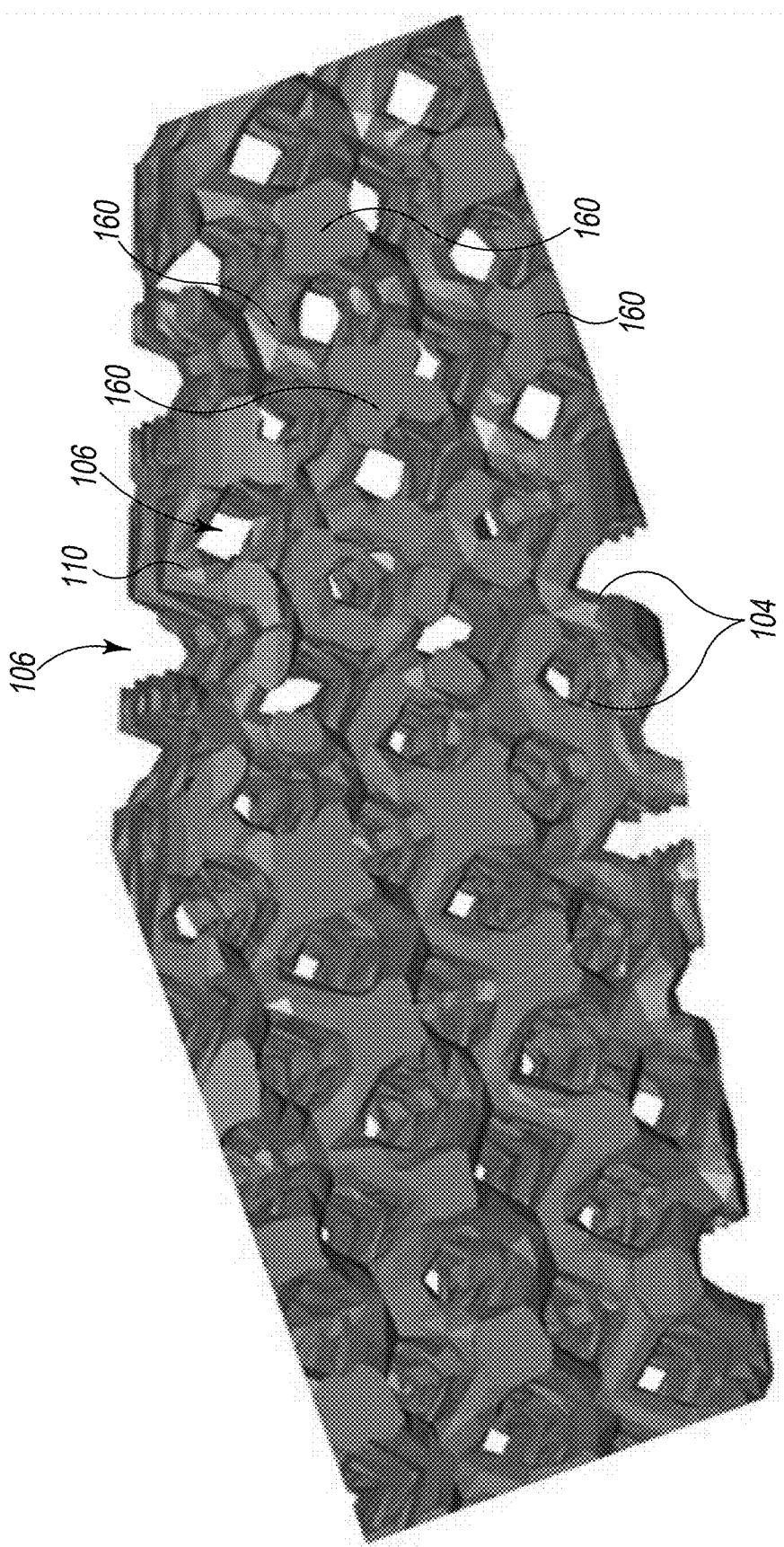
FIG. 3 is an enlarged perspective view of the frame shown in FIG. 2.

Referring now to FIG. 3, the interconnected beams 104 of the frame 100 define a plurality of polyhedrons 160. Because the polyhedrons 160 are interconnected, the beams 104 of one polyhedron 160 form part of one or more adjacent polyhedrons 160. The polyhedrons 160 are tessellated or stacked to fill three-dimensional space without voids between adjacent polyhedrons 160. In the illustrative embodiment, the only voids in the frame 100 are the openings 106 defined between the beams 104.

In the illustrative embodiment, each polyhedron 160 is an edge-transitive convex polyhedron. More specifically, each of the polyhedron 160 is a rhombic dodecahedron, which is understood to refer to a convex polyhedron with twelve congruent rhombic faces. The rhombic dodecahedron has twenty-four edges, and fourteen vertices of two different types. The unique geometry of the rhombic dodecahedron allows for an arrangement in which the polyhedrons 160 tessellate three-dimensional space to stabilize the frame 100 and resist tearing or failure of the implant 12.

Figure 4:
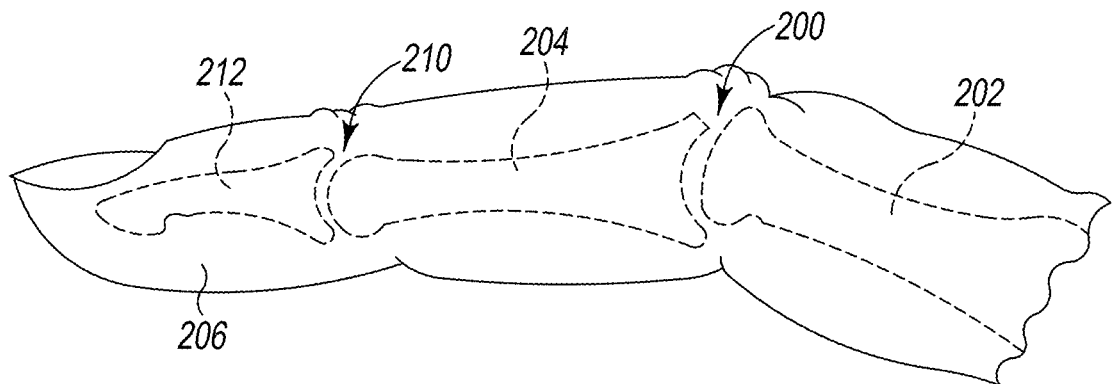
FIG. 4 is a side elevation view of the phalangeal bones of one finger.
Figure 5:
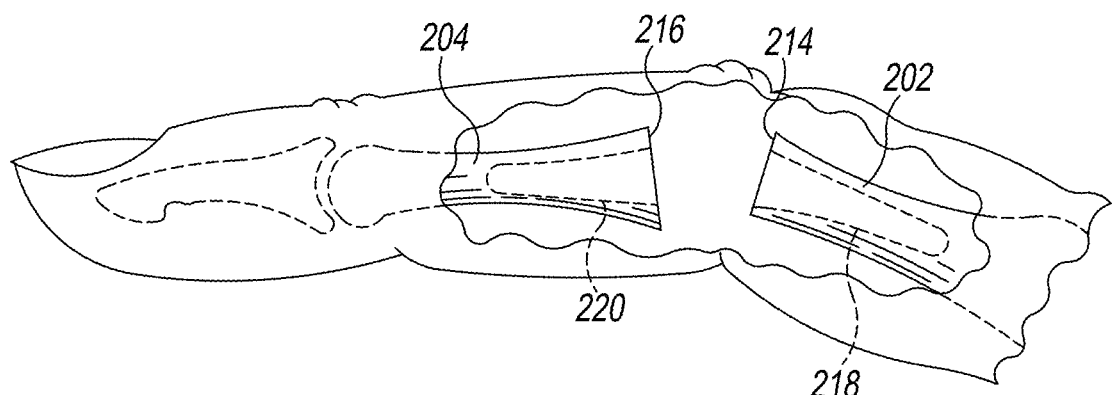
FIG. 5 is a side elevation view like FIG. 4 with the proximal interphalangeal joint removed.
Figure 6:
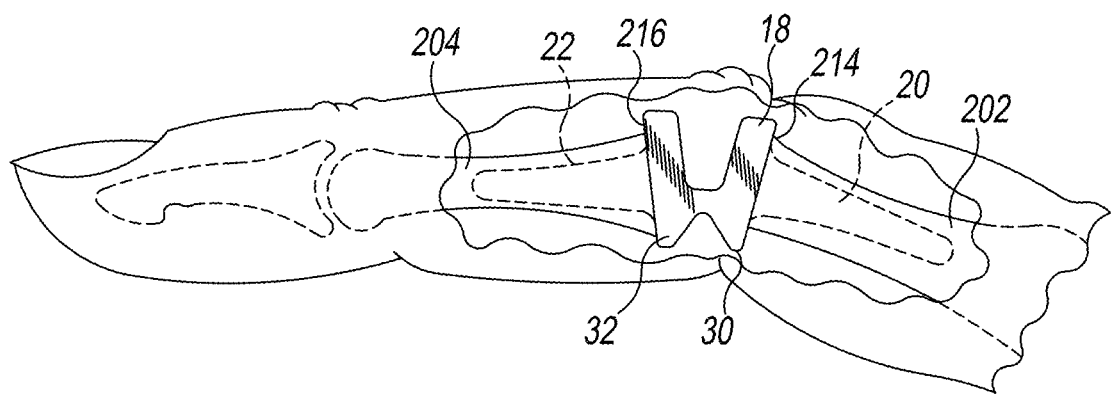
FIG. 6 is a side elevation view like FIG. 5 with the orthopaedic prosthesis of FIG. 1 implanted in the phalangeal bones.

Referring now to FIGS. 4-6, an exemplary surgical technique for implantation of the implant 12 is shown. As described above, a patient's interphalangeal joint 200 is defined between a proximal phalange 202 and a middle phalange 204 of the patient's finger 206. It should be appreciated that in other interphalangeal joint 210 is defined between the middle phalange 204 and a distal phalange 212 of the patient's finger 206. In illustrative embodiment, the surgical technique will focus on replacing the interphalangeal joint 200 of the patient's finger 206.

To do so, an incision is made over the interphalangeal joint 210. While the tendons are displaced, a surgeon or other user may use a cutting tool such as, for example, a micro-oscillating saw to resect a distal end 214 of the proximal phalange 202 and a proximal end 216 of the middle phalange 204 of the patient's finger 206, as shown in FIG. 5. A surgeon or other user may then use another cutting tool such as, for example, a surgical drill or reamer to define a bore 218 in the distal end 214 of the proximal phalange 202 sized to receive the proximal stem 20 of the implant 12. Another bore 220 is defined in the proximal end 216 of the middle phalange 204. The bore 220 is sized to receive the distal stem 22 of the implant 12.

The surgeon may then select an appropriately sized prosthesis 10 for implantation into the bones 202, 204. To implant the selected prosthesis 10, the surgeon may align the proximal tip 62 of the implant 12 with the distal opening of the bore 218 in the proximal phalange 202. The surgeon may then advance the proximal stem 20 of the implant 12 into the bore 218 and position the proximal wing 30 of the central component 18 in contact with the resected distal end 214 of the proximal phalange 202, as shown in FIG. 6. Similarly, the surgeon may align the distal tip 66 of the implant 12 with the proximal opening of the bore 220 in the middle phalange 204. The surgeon may then advance the distal stem 22 of the implant 12 into the bore 220 and position the distal wing 32 of the central component 18 in contact with the resected proximal end 216 of the middle phalange 204.

Figure 7:
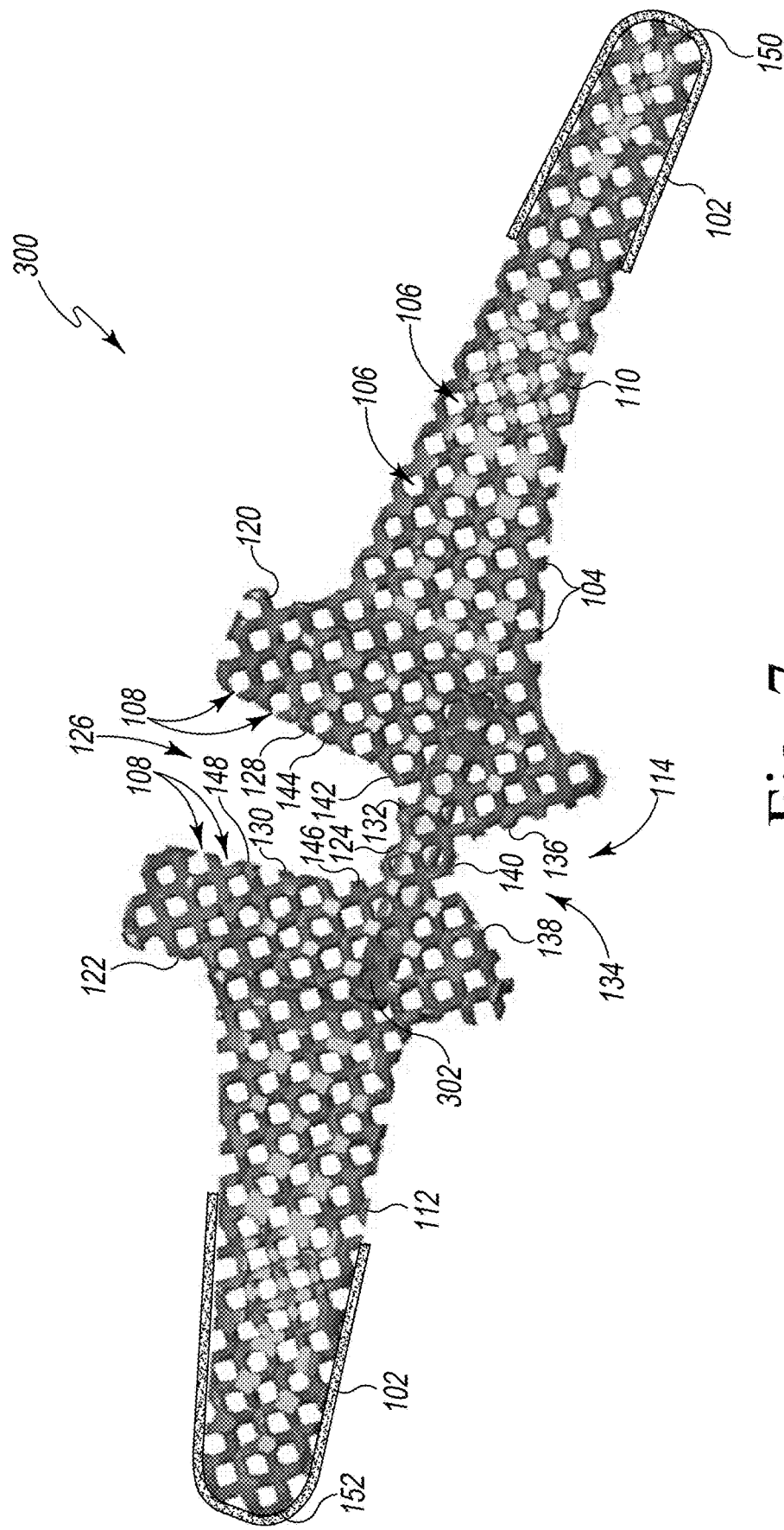
FIG. 7 is a perspective view of another embodiment of a frame of an orthopaedic prosthesis.

Referring now to FIG. 7, another embodiment of a frame (hereinafter frame 300) for the implant 12 is shown. The frame 300 may be used as an alternative to the frame 100 described above, and, like the frame 100, forms the basic structure that defines the geometry of the implant 12. The frame 300 also is also composed of the plurality of interconnected beams 104 that define a plurality of polyhedrons 160. As described above regarding the frame 100, the polyhedrons 160 are tessellated or stacked to fill three-dimensional space without voids between adjacent polyhedrons 160, and each polyhedron 160 is an edge-transitive convex polyhedron. The frame 300, like the frame 100, also includes a proximal arm 110, a distal arm 112, and a central body 114 that connects the proximal arm 110 to the distal arm 112.

As shown in FIG. 7, a reinforcement plate 302 is positioned in the central body 114 of the frame 300 between the grooves 126, 134. The plate 302 extends from the medial side to the lateral side of the central body 114 and is configured to reinforce and strengthen the bridge 124 connecting the proximal wing 120 to the distal wing 122 of the central body 114. In the illustrative embodiment, the plate 302 is polygonal with rectangular surfaces that face the grooves 126, 134. In other embodiments, the plate may have an oval cross-section or take other geometric shapes. In still other embodiments, the plate may be embodied as a plurality of rods or shafts positioned in the bridge 124.

In the illustrative embodiment, the frame 300 and the reinforcement plate 302 are formed by stereolithography. It should be appreciated that other forms of 3-D printing technology such as, for example, optical fabrication, photo-solidification, or resin printing may be used to fabricate the frame 300 and plate 302. In other embodiments, the frame 100 or 300 and plate 302 may be formed from a metallic material using a 3-D printing process.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. A method of implanting an orthopaedic prosthesis, comprising:
removing a portion of a first phalangeal bone of a patient, a portion of second phalangeal bone, and a natural joint between the first phalangeal bone and the second phalangeal bone,
inserting a proximal end of an orthopaedic prosthesis into the first phalangeal bone, and
inserting a distal end of the orthopaedic prosthesis into the second phalangeal bone,
wherein the orthopaedic prosthesis includes an inner frame comprising a plurality of tessellated polyhedrons, wherein the plurality of tessellated polyhedrons of the inner frame define an open-cell structure, and wherein the open-cell structure comprises a dorsal surface, a palmar surface, and a three-dimensional inner open-cell structure that extends between the dorsal surface and the palmar surface, wherein the open-cell structure includes a central joint connecting the proximal end and the distal end, a first groove formed in a dorsal end of the central joint, and a second groove formed in a palmar end of the central joint positioned opposite the first groove to permit flexion motion between the proximal end of the orthopaedic prosthesis and the distal end of the orthopaedic prosthesis, and an outer shell that encases the inner frame, the outer shell extending from the proximal end to the distal end over the inner frame including the central joint.

2. The method of claim 1, wherein inserting the proximal end of the orthopaedic prosthesis includes engaging the outer shell of the orthopaedic prosthesis with the patient's tissue.

3. The method of claim 1, wherein inserting the distal end of the orthopaedic prosthesis includes engaging the outer shell of the orthopaedic prosthesis with the patient's tissue.

4. The method of claim 1, further comprising making the inner frame via a stereolithographic process.

5. The method of claim 4, further comprising coating the inner frame with the outer shell.

6. The method of claim 1, wherein the plurality of tessellated polyhedrons includes rhombic dodecahedrons.

7. The method of claim 1, wherein the second groove extends from a palmar opening formed in the palmar end of the central joint, wherein the second groove is at least partially defined by a planar palmar surface extending from an arcuate palmar surface to the palmar opening.

8. The method of claim 7, wherein wherein the open-cell structure includes the proximal end and the distal end.

* * * * *